US00PP32035P2

(12) United States Plant Patent
Dirr

(10) Patent No.: US PP32,035 P2
(45) Date of Patent: Aug. 4, 2020

(54) HOLLY PLANT NAMED 'MAD-IC1'

(50) Latin Name: *Ilex crenata*
Varietal Denomination: MAD-IC1

(71) Applicant: University of Georgia Research Foundation, Inc., Athens, GA (US)

(72) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,551

(22) Filed: Oct. 29, 2019

(51) Int. Cl.
*A01H 5/00* (2018.01)

(52) U.S. Cl.
USPC ..... Plt./247

(58) Field of Classification Search
USPC ..... Plt./247
CPC ..... A01H 5/00
See application file for complete search history.

*Primary Examiner* — Annette H Para

(74) *Attorney, Agent, or Firm* — Klarquist Sparkman, LLP

(57) ABSTRACT

A new cultivar of *Ilex crenata* plant named MAD-IC1, that is characterized by its broad columnar-fastigiate habit, its exceptional strong branches that do not splay, its coriaceous lustrous dark green pest-resistant foliage, and its propensity to produce shiny black fruits if a suitable pollinator is in proximity.

4 Drawing Sheets

Genus and species: *Ilex crenata.*

Variety denomination: The new *Ilex crenata* claimed is of the cultivar denominated 'MAD-IC1'.

BACKGROUND OF THE INVENTION

The present invention relates to a new and distinct cultivar of *Ilex crenata* and will be referred to hereafter by its cultivar name 'MAD-IC1'. 'MAD-IC1' is a new cultivar of holly grown for use as a landscape and container ornamental plant.

The new cultivar of *Ilex* arose from a breeding program conducted by the inventor. 'MAD-IC1' originated as a seedling from seed derived from open-pollinated *Ilex crenata* 'Sky Pencil' (not patented). Male parentage is unknown. 'MAD-IC1' was selected as a single unique plant in 2007 from among the resultant seedlings.

Asexual propagation of the new cultivar was first accomplished by greenwood cuttings (semi-hardwood) in a nursery in Watkinsville, Ga. in 2008. Asexual propagation by semi-hardwood cuttings has determined that the characteristics of the new cultivar are stable and are reproduced true-to-type in successive generations.

SUMMARY OF THE INVENTION

The following traits have been observed repeatedly and represent the characteristics of the new cultivar. These attributes distinguish 'MAD-IC1' as a unique cultivar of *Ilex.*

1. 'MAD-IC1' exhibits a broad columnar-fastigiate habit
2. 'MAD-IC1' develops exceptionally strong branches that do not splay
3. 'MAD-IC1' exhibits pest resistant, lustrous dark green, coriaceous leaves which do not discolor in winter

COMPARISON TO OTHER VARIETIES

1. 'MAD-IC1' differs from 'PIIIC-1' (U.S. Plant Pat. No. 29,578) as 'MAD-IC1' is a female and produces shiny black fruit; and 'PIIIG-1' only produces male flowers 2. 'MAD-IC1' is about twice as wide as 'PIIIC-1' at maturity
3. 'MAD-IC1' develops stronger branches than 'PIIIC-1'
4. The branches of 'MAD-IC1' do not splay like those of its parent plant 'Sky Pencil'

DETAILED BOTANICAL DESCRIPTION

Figure 1:
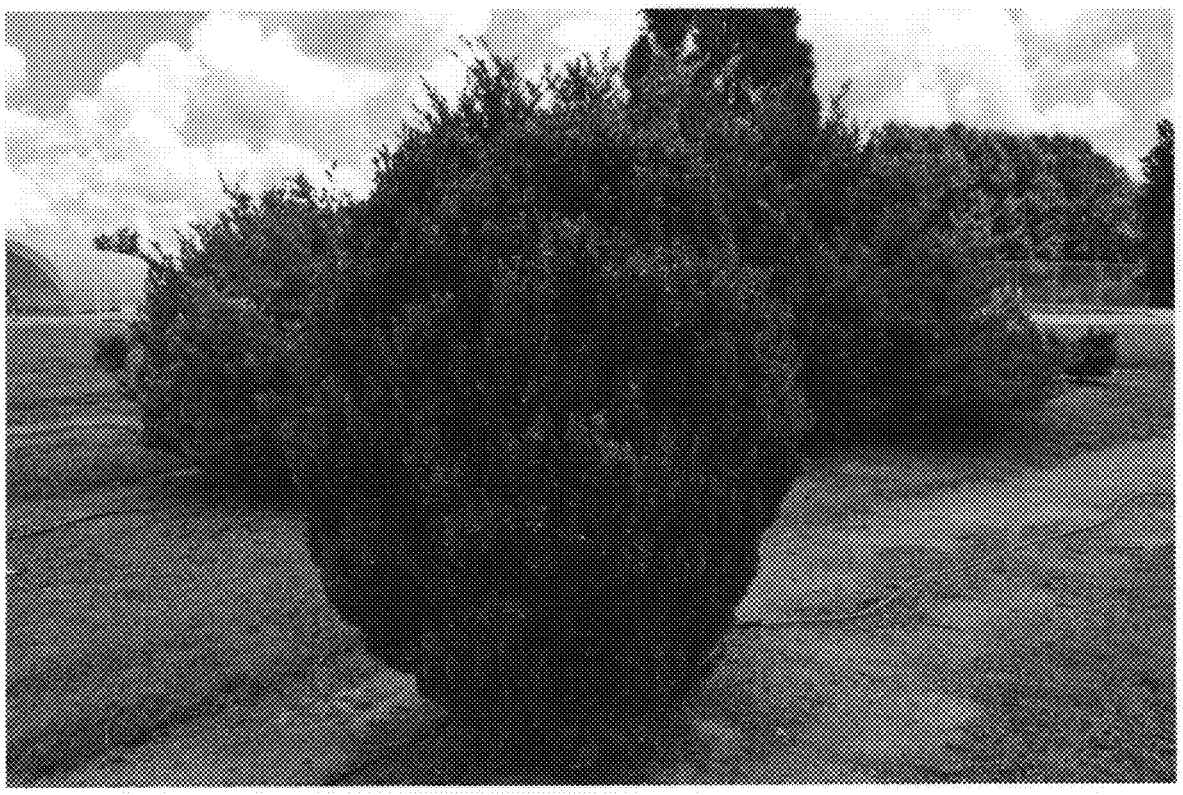
FIGS. 1 and 2 illustrate the overall appearance and distinct characteristics of the 13-year-old plant of the new cultivar as grown in the ground in Watkinsville, Ga.
Figure 2:
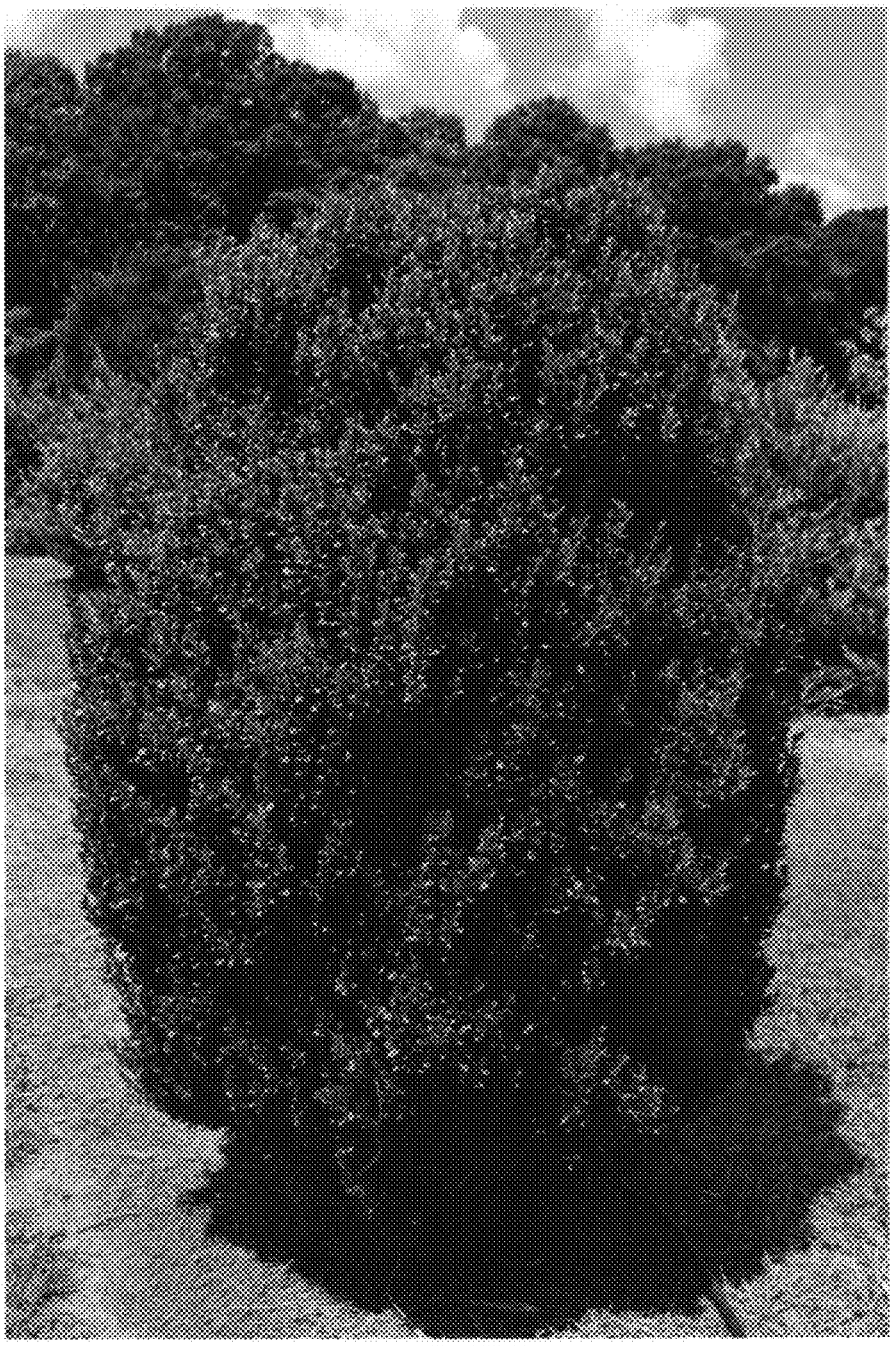
Figure 3:
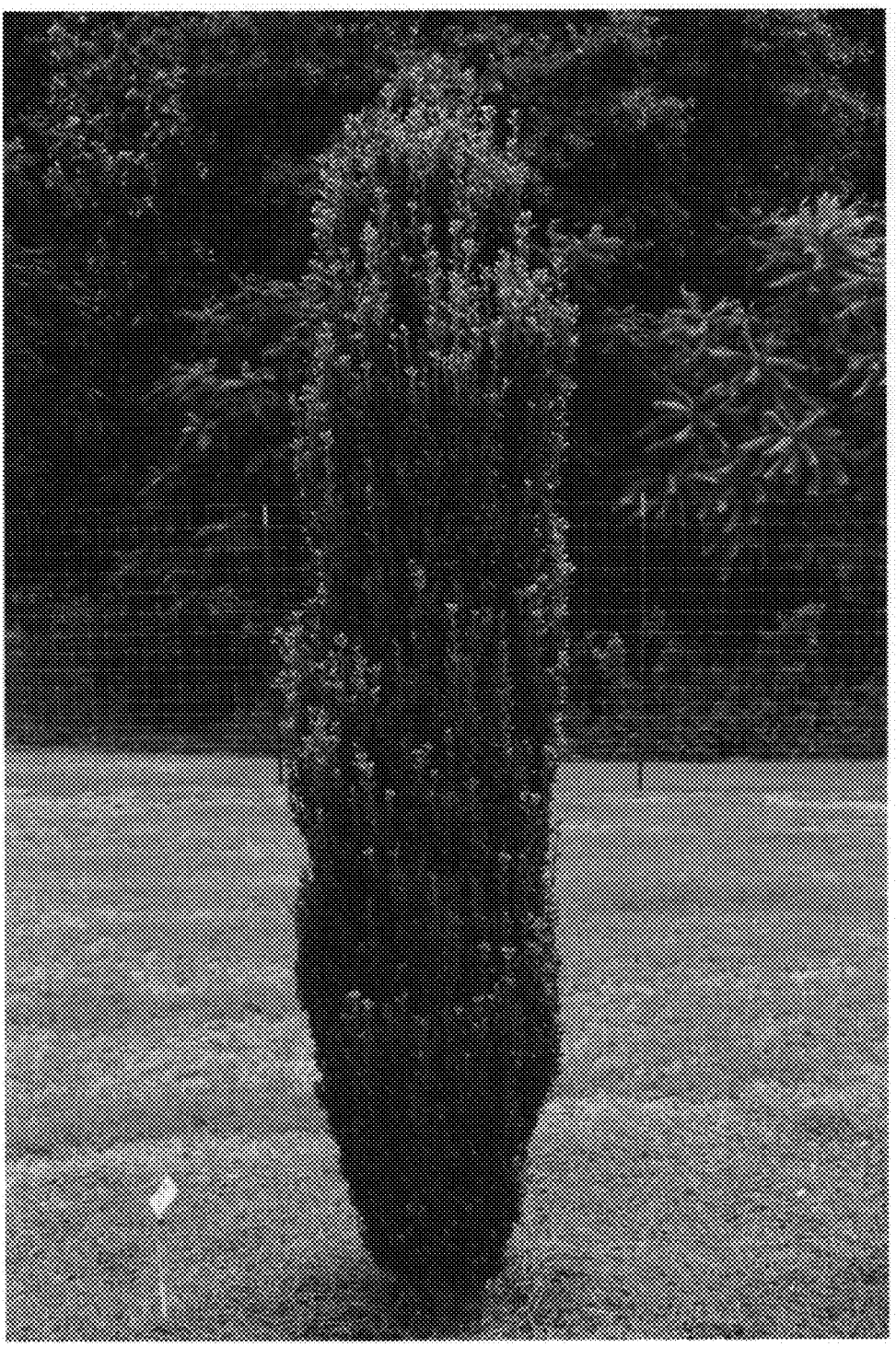
FIG. 3 shows 'PIIIC-1' for comparison.
Figure 4:
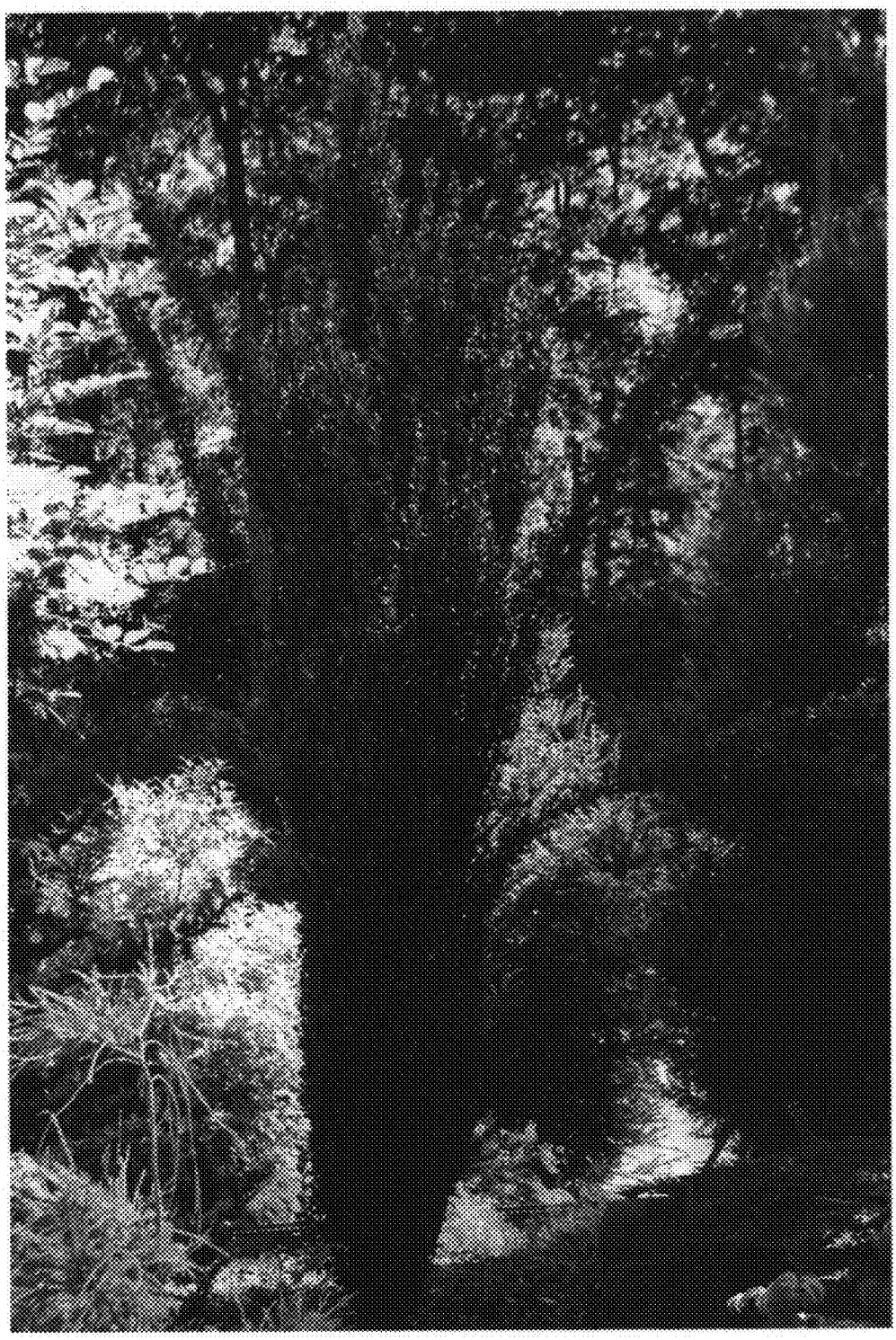
FIG. 4 shows 'Sky Pencil' for comparison.

The following is a detailed description of the original 13-year-old plant as grown in the ground in Watkinsville, Ga. The phenotype of the new cultivar may vary with permutations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary significance are used.

Habit: Broad, uniformly columnar-fastigiate plant with numerous, small lateral branches.

Size of plant: 13 year old plant.

A. *Height.*—203 cm (2.03 M).
B. *Width.*—119 cm (1.9 M).

Branch:

A. *Color.*—137D.
B. *Length.*—14 cm.
C. *Diameter.*—3 mm.
D. *Texture/pubescence.*—Smooth and glabrous.
E. *Shape.*—Rounded.
F. *Odor (of bruised stem).*—Slightly fetid.
G. *Internode length.*—1.2 cm.

Leaf:

A. *Type*.—Simple pinnate.

B. *Color* (*RHS*).—1. Upper: Emerging leaves — 137A; Mature leaves — 139A. 2. Lower: Emerging leaves — 138A. Mature leaves — 137B.

C. *Mature size* (*L×W*).—2.5 cm×1.2 cm.

D. *Apex*.—Acute.

E. *Base*.—Cuneate.

F. *Margin*.—Entire at base with crenate gland tipped serrations toward apex.

G. *Shape*.—Elliptical and slightly convex.

H. *Lobes* (*present/absent*).—None.

I. *Texture/pubescence*.—Fine/glabrous.

J. *Arrangement on stem*.—Alternate.

K. *Venation*.—Pinnate, color; 139A on upper surface and 137B on lower surface.

L. *Texture*.—Lustrous, glabrous on upper surface. Lower surface is dull and coriaceous.

M. *Odor when crushed*.—None.

Petiole:

A. *Length*.—3 mm.

B. *Shape*.—Grooved in center on upper or adaxial side; rounded on lower or abaxial side.

C. *Color* (*RHS*).—139C.

D. *Texture/pubescence*.—Shiny, smooth, and glabrous.

E. *Diameter*.—1 mm.

Inflorescence:

A. *Type*.—Single, solitary flowers produced in axils of leaves on first year shoots.

B. *Number per plant*.—Numerous; estimate approx. 500 on original plant.

C. *Longevity*.—10-14 days.

Flower:

A. *Number per Inflorescence*.—1.

B. *Size* (*L×W*).—6 mm×6 mm.

C. *Fragrance*.—None.

D. *Bud*.—1. Size (L×W): 1.5 mm×1.5 mm. 2. Shape: Rounded in outline. 3. Color (RHS): 139C.

E. *Petals*.—1. Number: 4. 2. Size (L×W): 3 mm×2 mm. 3. Shape: Ovate. 4. Apex: Obtuse. 5. Base: Rounded. 6. Margin: Entire. 7. Color at Peak of Bloom (RHS): Upper and lower surface 155D. 8. Texture/Pubescence: Smooth and glabrous on upper and lower surfaces.

F. *Pedicels*.—1. Color (RHS): 145A. 2. Texture/Pubescence: Smooth, glabrous surface. 3. Length: 2 mm. 4. Strength: Firm.

G. *Sepals*.—1. Number: 4-lobed. 2. Size (L×W): 3 mm×3 mm. 3. Shape: Rounded apex. 4. Texture/Pubescence: Smooth and glabrous. 5. Color (RHS): 144C.

Fruits: Shiny black fruit.

Seeds:

1. *Number*.—4 pyrenes.
2. *Size* (*L×W*).—5 mm×3 mm.
3. *Shape*.—Oblong, ellipsoidal.
4. *Color*.—199D.
5. *Texture/pubescence*.—Abaxially smooth, striate, leathery endocarp.

What is claimed is:

1. A new and distinct cultivar of the *Ilex* plant named 'MAD-IC1' as illustrated and described herein.

* * * * *